United States Patent [19]

Tasaka et al.

[11] Patent Number: 4,554,382

[45] Date of Patent: Nov. 19, 1985

[54] DEHYDRATING DECOMPOSITION PROCESS FOR PREPARING CARBONYL COMPOUND

[75] Inventors: Yoshihiro Tasaka; Toshihiro Nakamichi, both of Kamifukuoka; Yutaka Katsuhara, Kawagoe, all of Japan

[73] Assignee: Central Glass Company Limited, Ube, Japan

[21] Appl. No.: 595,038

[22] Filed: Mar. 29, 1984

[30] Foreign Application Priority Data

Mar. 30, 1983 [JP] Japan .................................. 58-52668

[51] Int. Cl.$^4$ .............................................. C07C 45/52
[52] U.S. Cl. ...................................... 568/404; 568/486
[58] Field of Search .............. 568/404, 405, 486, 419, 568/495

[56] References Cited

U.S. PATENT DOCUMENTS

| | | | |
|---|---|---|---|
| 2,901,514 | 8/1959 | Drysdale | 568/419 |
| 3,919,328 | 11/1975 | Gutierrey et al. | 568/405 |
| 3,928,459 | 12/1975 | Mercier | 568/486 |
| 4,304,927 | 12/1981 | Krespan | 568/404 |

OTHER PUBLICATIONS

Patai, The Chemistry of the Carbonyl Group, Interscience Publns, pp. 188–192, (1966).

Primary Examiner—James H. Reamer
Attorney, Agent, or Firm—Fleit, Jacobson, Cohn & Price

[57] ABSTRACT

Dehydrating decomposition of compound (I), i.e. gem-diol, hemi-acetal or hemi-ketal, by contact with sulfuric acid gives a carbonyl compound (II).

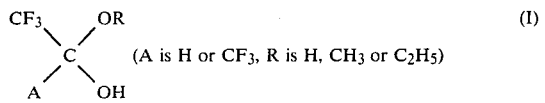

(A is H or CF$_3$, R is H, CH$_3$ or C$_2$H$_5$)

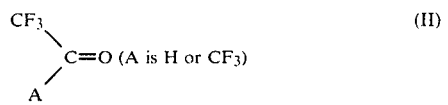

C=O (A is H or CF$_3$)

Disclosed is a two-stage process in which the first stage is the contact of compound (I) with sulfuric acid at 90°–140° C. so as to partly decompose and dehydrate the compound (I), permitting the concentration of sulfuric acid to become lower than 93 wt. % but not lower than 65 wt. %, and the second stage is the contact of the product of the first-stage reaction with concentrated sulfuric acid at a temperature not higher than 60° C., preventing the concentration of sulfuric acid from becoming lower than 93 wt %. For example, hexafluoroacetone is obtained from a hydrate thereof by this process using only a small amount of sulfuric acid.

5 Claims, 1 Drawing Figure

U.S. Patent                Nov. 19, 1985                4,554,382
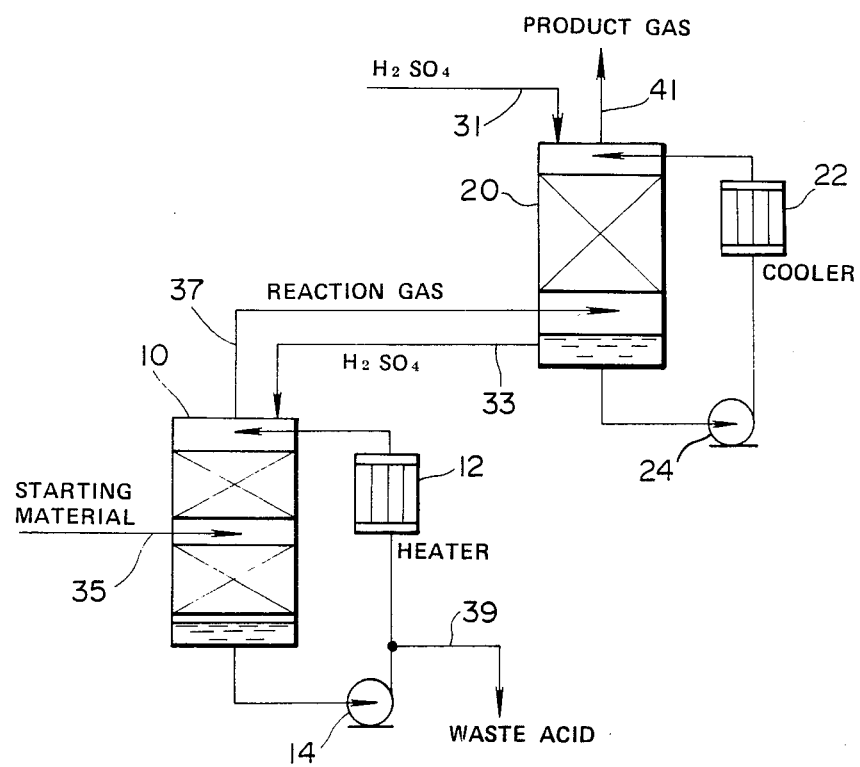

4,554,382

DEHYDRATING DECOMPOSITION PROCESS FOR PREPARING CARBONYL COMPOUND

BACKGROUND OF THE INVENTION

This invention relates to an improved process of preparing a fluorinated carbonyl compound, which is expressed by the general formula (II), by dehydrating decomposition of a gem-diol, hemi-acetal or hemi-ketal, which is expressed by the general formula (I), using sulfuric acid as a decomposing and dehydrating agent.

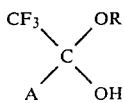

where A represents H or $CF_3$, and R represents H, $CH_3$ or $C_2H_5$.

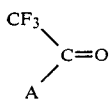

where A represents H or $CF_3$.

For the purpose of storing a fluorinated carbonyl compound which is expressed by the general formula (II) and has a boiling point below room temperature in a stable state, it has been put into practice to convert the carbonyl compound into a gem-diol, hemi-acetal or hemi-ketal of the general formula (I). The alcoholizing or acetalizing reaction is represented by the following equation (1).

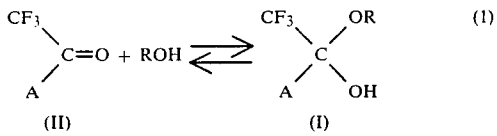

Since the reaction of Equation (1) is reversible, the carbonyl compound (II) can be isolated in the initial form by the dehydrating decomposition of the gem-diol, hemi-acetal or hemi-ketal (I) preparatory to the use of the carbonyl compound as a starting material in various synthesis reactions. The decomposition of the compound (I) as the reverse reaction of Equation (1) is customarily accomplished by making the compound (I) contact with concentrated sulfuric acid at a relatively high temperature, i.e. at a temperature above 90° C. However, it is a disadvantage of this method from an economical point of view that a very large amount of concentrated sulfuric acid needs to be used.

Hexafluoroacetone $(CF_3)_2C=O$ (abbreviated to HFA) can be named as a typical example of fluorinated carbonyl compounds of the formula (II). HFA is very high in reactivities and has wide uses as intermediates of medicines and agricultural chemicals. Under the atmospheric pressure, HFA is a gaseous compound having a boiling point of $-28°$ C. and reacts rapidly with water to form monohydrate (will be abbreviated to HFA-1W), which is regarded as a gem-diol $(CF_3)_2C(OH)_2$, as represented by the following equation.

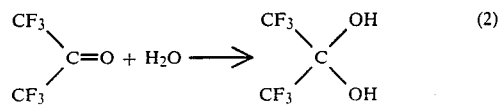

HFA-1W is a solid in the form of white needle-shaped crystals having a melting point of 47° C. and readily dissolves in water. When HFA-1W is dissolved in such an amount of water that the mole ratio of water to HFA is about 3, the solution becomes an azeotropic composition (will be represented by HFA-3W) of which the boiling point is 106° C. under the atmospheric pressure.

Since HFA is a noxious gas having a characteristically irritating smell and it is difficult to handle gaseous HFA as an industrial material, it is usual to transport and store HFA in the state of HFA-3W which is a liquid convenient for handling.

Preparatory to a reaction process using HFA, the stored HAF-3W can be decomposed and dehydrated with concentrated sulfuric acid usually at temperatures in the range from 90° to 120° C. It is ensured that the reaction proceeds in the presence of concentrated sulfuric acid, firstly because the solubility of anhydrous HFA in sulfuric acid increases as the concentration of sulfuric acid lowers and secondly because lowering in the concentration of sulfuric acid causes a rise in the vapor pressure of water on sulfuric acid so that the intended dehydration becomes incomplete with the result of precipitation of the gem-diol or HAF-1W on the wall of the reactor. It is conceivable to lower the reaction temperature to thereby lower the vapor pressure of water, but it is impracticable to lower the reaction temperature below 90° C. from an industrial point of view because of extreme lowering of the rate of the decomposition reaction. For these reasons the reaction is carried out with best care not to lower the concentration of sulfuric acid, and therefore a very large amount of sulfuric acid must be used.

SUMMARY OF THE INVENTION

It is an object of the present invention to provide an improved process of preparing a carbonyl compound, which is expressed by the general formula (II) and has a boiling point below room temperature under the atmospheric pressure, by dehydrating decomposition of a gem-diol, hemi-acetal or hemi-ketal which is expressed by the general formula (I), with a view to decreasing the quantity of sulfuric acid used for the dehydrating decomposition.

A process according to the invention for preparing a carbonyl compound, which is expressed by the general formula (II) and has a boiling point below room temperature under the atmospheric pressure, is a two-stage process comprising the steps of (a) at the first stage, making a gem-diol, hemi-acetal or hemi-ketal expressed by the general formula (I) contact with the sulfuric acid at a temperature in the range from 90° to 140° C. so as to partly decompose and dehydrate the gem-diol, hemi-acetal or hemi-ketal, permitting the concentration of the sulfuric acid to become lower than 93% by weight but not lower than 65% by weight, and (b) at the second stage, making the product of the reaction at step (a) contact with concentrated sulfuric acid at a temperature not higher than 60° C., preventing the concentration of the concentrated sulfuric acid from becoming lower than 93% by weight.

Preferably, the reaction at step (a) is carried out at a temperature in the range from 120° to 130° C. while preventing the concentration of sulfuric acid from becoming lower than 78% by weight, and the reaction at step (b) is carried out at a temperature not higher than 30° C. while preventing the concentration of concentrated sulfuric acid from becoming lower than 95% by weight.

In the process according to the invention, the dehydrating decomposition is carried out without adhering to the use of concentrated sulfuric acid at the initial stage where a large amount of water or alcohol is liberated by the decomposition reaction, and without intending to convert the entire amount of the starting material into the carbonyl compound at this stage. At the later stage where only a small amount of organic material is decomposed it is required to use concentrated sulfuric acid, but the reaction system at this stage is maintained at a relatively low temperature. Accordingly, vapor pressure of water on sulfuric acid in the second-stage reaction system becomes very low, which is favorable for the efficiency of dehydration. Due to the reduced temperature the solubility of the carbonyl compound in sulfuric acid in the second-stage reaction system will somewhat increase, but it is possible to recover almost the entire amount of the dissolved organic compound because the sulfuric acid gradually extracted from the second-stage reaction system can be fed to the first-stage reaction system as a make-up.

A principal advantage of the process according to the invention is the possibility of greatly decreasing the amount of sulfuric acid used to obtain a unit quantity of the intended carbonyl compound.

In practice, this process can be performed either batchwise or continuously.

For example, this process is very suited to the conversion of HFA-3W, i.e. aqueous solution of a gem-diol $(CF_3)_2C(OH)_2$, to anhydrous HFA gas on an industrial scale.

BRIEF DESCRIPTION OF THE DRAWING

The single FIGURE is a flow diagram of a continuous decomposition process according to the invention.

DESCRIPTION OF THE PREFERRED EMBODIMENTS

The present invention can be put into practice as a continuous process, which will be described with reference to the FIGURE in the drawing by way of example.

The illustrated reaction apparatus includes two reactors: first-stage reactor 10 provided with a heater 12 and a circulating pump 14 and second-stage reactor 20 provided with a cooler 22 and a circulating pump 24. Concentrated sulfuric acid indicated at 31 is continuously supplied to the second-stage reactor 20, while an overflown portion of sulfuric acid 33 flows from the second-stage reactor 20 to enter the first-stage reactor 10. The heater 12 is operated so as to maintain the temperature in the first-stage reactor 10 at 90°–140° C. and preferably at 120°–130° C., and the cooler 22 is operated so as to maintain the temperature in the second-stage reactor 20 below 60° C. (inclusive) and preferably below 30° C. (inclusive). A gem-diol, hemi-acetal or hemi-ketal of the formula (I) indicated at 35 is continuously supplied to the first-stage reactor 10. The material 35 of the formula (I) may be in a state mixed with excess water in the case of a gem-diol or excess alcohol in the case of a hemi-acetal or hemi-ketal. For example, the material 35 is an azeotropic solution referred to as HAF-3W.

In the first-stage reactor 10 the concentration of sulfuric acid needs not to remain at the level of so-called concentrated sulfuric acid. More particularly, in this reactor 10 it suffices that the concentration of sulfuric acid is 65 wt%, and preferably 78 wt%, at the lowest. In the second-stage reactor 20 the concentration of sulfuric acid should be at least 93 wt%, and preferably 95 wt% or above.

The starting material 35 introduced into the first-stage reactor 10, HAF-3W for example, is heated and comes into contact with heated sulfuric acid to undergo dehydrating decomposition. The greater portion of the supplied HAF-3W is decomposed and dehydrated to HFA within the first-stage reactor 10, so that the reaction gas 37 flowing out of the first-stage reactor 10 to enter the second-stage reactor 20 is mostly HFA gas mixed with a small amount of water vapor. A small portion of HFA-3W supplied to the first-stage reactor 10 remains hydrated and accompanies the reaction gas 37 in the form of HFA-1W.

Waste sulfuric acid 39 is continuously discharged from the first-stage reactor 10. A small amount of organic compound dissolved in the waste sulfuric acid, such as HFA, can easily and entirely be recovered by raising the concentration of the acid using fuming sulfuric acid.

In the second-stage reactor 20 the reaction gas 37 comes into contact with concentrated sulfuric acid at a relatively low temperature to undergo complete dehydration. Simultaneously, HFA-1W contained in the reaction gas 37 is completely decomposed and dehydrated with concentrated sulfuric acid. Consequently, substantially pure HFA gas flows out of the second-stage reactor 20 as product gas indicated at 41. Sulfuric acid somewhat diluted with absorbed water is continuously discharged from the second-stage reactor 20 and fed to the first-stage reactor 10 as a make-up. Therefore, the required high level of sulfuric acid concentration is maintained in the second-stage reactor 20, and HFA dissolved in sulfuric acid within the second-stage reactor 20 can also be recovered from the first-stage reactor 10.

Either packed towers or tray towers can be used as the first-stage and second-stage reactors 10 and 20. The manner of contact of the starting material 35 or the first-stage reaction gas with sulfuric acid may be either parallel-current contact or counter-current contact. In the case of parallel-current contact, both the organic material and sulfuric acid are flown upward. In the case of counter-current contact, sulfuric acid is flown downward from the top section of the tower and the organic material is introduced into the tower at an intermediate section thereof. Instead of using two towers, it is also possible to carry out both the first-stage and second-stage reactions within a single tower. In that case, the tower is divided into a lower section in which heated sulfuric acid is circulated to carry out the first-stage reaction and an upper section in which concentrated sulfuric acid is circulated at a relatively low temperature.

As to the rate of the dehydrating decomposition reaction, it is suitable that the linear velocity of the organic gas in each tower is in the range from 0.1 to 10 cm/sec, and preferably from 0.5 to 4 cm/sec, calculating at N.T.P. and that the stay time of the organic gas is in the range from 5 to 200 sec and preferably from 20 to 50 sec.

If desired, an auxiliary decomposing and dehydrating agent such as polyphosphate or phosphorus pentoxide may be used together with sulfuric acid.

The invention will further be illustrated by the following nonlimitative examples.

EXAMPLE 1

This example relates to the dehydrating decomposition of HFA-3W.

A glass cylinder 25 mm in diameter and 300 mm in height was used as the first-stage reactor and packed with glass beads which were 2 mm in diameter. As the second-stage reactor, use was made of a gas absorption tube which was 70 mm in diameter and 250 mm in height and provided with glass bubbler. The first-stage reactor body and the piping between the first-stage and second-stage reactors were provided with heating and heat-insulating means.

In a 2-liter round bottom flask, 1400 ml of 98 wt% sulfuric acid was heated to 130° C. on oil bath. The heated sulfuric acid was fed to the first-stage reactor at a rate of 176 g/min to flow into the reactor by the inlet at the bottom and return to the flask by overflow from the top of the reactor. Meanwhile, 700 ml of 98% sulfuric acid was charged in the second-stage reactor. A Dimroth condenser using ice water was provided at the outlet of the second-stage reactor so that refined HFA gas flowing out of the reactor could be absorbed in water.

When the temperature in the first-stage reactor rose up to 125° C., commenced was the feed of a mixed liquid of HFA-3W and heated sulfuric acid at a rate of 3.76 g/min by the inlet at the bottom of the reactor. In this manner, the dehydrating decomposition reaction was continued without varying the reaction temperature and the rate of the feed of the mixed liquid.

After the lapse of 17 hr from the start of the reaction, precipitation of HFA-1W was observed in the condenser, indicating that the decomposing-dehydrating capability of the used sulfuric acid reached the limit. At this stage the concentration of gem-diol, i.e. HFA-1W, in the discharged gas was 100 ppm by volume in terms of the water. (Also in the succeeding example and comparative experiments, this value for the concentration of gem-diol was taken as the limit of the reaction in evaluating the respective processes.) By that time, the total amount of the feed of HFA-3W reached 3835 g (2894 g as HFA) and the quantity of recovered HFA was 2820 g, so that the recovery efficiency was 97.4% by weight. In the first-stage reactor sulfuric acid had been diluted to a concentration of 71.4 wt% and in the second-stage reactor to a concentration of 93.4 wt%. In this process 1.36 kg of sulfuric acid was used per 1 kg of HFA.

Table 1 shows experimental data obtained in the course of the reaction in Example 1 by measurements at suitable time intervals.

TABLE 1

| Reaction Temperature (°C.) | | Feed of HFA-3W, cumulative (g) | Recovery of HFA (wt %) | Solubility of HFA in Acid (wt. ppm) | | Concentration of Sulfuric Acid (wt %) | |
|---|---|---|---|---|---|---|---|
| 1st stage | 2nd stage | | | 1st stage | 2nd stage | 1st stage | 2nd stage |
| 128 | 44 | 680 | 99.8 | 500 | trace | 91.8 | 97.4 |
| " | 53 | 1299 | 99.6 | 1400 | 800 | 85.9 | 96.9 |
| " | 50 | 1902 | 99.3 | 2000 | 1100 | 82.6 | 96.4 |
| " | " | 2538 | 99.5 | 3700 | 1700 | 78.7 | 95.6 |
| " | " | 3125 | 99.1 | 7900 | 2800 | 75.1 | 94.6 |
| " | " | 3835 | 97.4 | 23100 | 6000 | 71.3 | 93.4 |

COMPARATIVE EXPERIMENT 1

HFA-3W was subjected to the dehydrating decomposition reaction in the same apparatus and under the same conditions as in Example 1 except that sulfuric acid was absent in the second-stage reactor. That is, the reaction took place only in the first-stage reactor.

After the lapse of 1.5 hr from the start of the reaction, precipitation of HFA-1W was observed in the condenser. By that time, the total amount of the feed of HFA-3W was 342 g (258 g as HFA) and the quantity of recovered HFA was 254 g, so that the recovery efficiency was 98.4% by weight. The concentration of sulfuric acid had lowered to 94.9 wt%, and the solubility of HFA in the acid reached 1500 ppm by weight. In this case 10.1 kg of sulfuric acid was used per 1 kg of HFA.

COMPARATIVE EXPERIMENT 2

As a sole modification of Comparative Experiment 1, the reaction temperature was lowered to 30° C.

After the lapse of 2.3 hr from the start of the reaction, precipitation of HFA-1W was observed in the condenser. By that time the total amount of the feed of HFA-3W was 515 g (389 g as HFA) and the quantity of recovered HFA was 332 g, so that the recovery efficiency was 83.3% by weight. The concentration of sulfuric acid had lowered to 93.4 wt%, and the solubility of HFA in the acid reached 21,300 ppm by weight. In this case 7.7 kg of sulfuric acid was used per 1 kg of HFA.

EXAMPLE 2

The two-stage apparatus described in Example 1 was used for continuously carrying out the dehydrating decomposition of HFA-3W.

In this case, 1400 ml of 78 wt% of sulfuric acid was charged in the round bottom flask provided to the first-stage reactor and 700 ml of 95 wt% sulfuric acid into the second-stage reactor. The first-stage reactor was heated so as to raise the liquid temperature up to 130° C.

The reaction was started by continuously feeding HFA-3W at a rate of 3.76 g/min to the first-stage reactor. At the same time, flow control valves in the apparatus were adjusted so as to circulate sulfuric acid from the bottom of the second-stage reactor to the round bottom flask of the first-stage reactor at a rate of 3.64 g/min, to withdraw diluted sulfuric acid from the round bottom flask at a rate of 4.54 g/min and to feed 95 wt% sulfuric acid to the second-stage reactor as make-up at a rate of 3.59 g/min.

The feed of HFA-3W was continued for 20 hr, without observing precipitation of HFA-1W in the condenser. The solubility of HFA in the waste sulfuric acid was 4000 ppm by weight.

EXAMPLE 3

Using the two-stage apparatus described in Example 1, reaction between sulfuric acid and trifluoroacetoaldehyde methyl hemi-acetal $CF_3CH(OH)OCH_3$ was carried out under the same reaction conditions as in Example 1.

In this case, the decomposing-dehydrating capability of sulfuric acid was judged to have reached the limit when gem-diol of trifluoroacetoaldehyde $CF_3CH(OH)_2$ (m.p. 93° C.) began to precipitate.

After the lapse of 32 hr from the start of the reaction, $CF_3CH(OH)_2$ began to precipitate in the condenser. At that time the concentration of sulfuric acid in the first-stage reactor was 72.0 wt%, and that in the second-stage reactor was 93.6 wt%. By that time the total amount of the feed of the hemi-acetal reached 7219 g (5442 g as $CF_3CHO$) and the quantity of recovered $CF_3CHO$ was 5371 g, so that the recovery efficiency was 98.7% by weight. In this case, 0.72 kg of sulfuric acid was used per 1 kg of the hemi-acetal.

COMPARATIVE EXPERIMENT 3

The hemi-acetal $CF_3CH(OH)OCH_3$ was subjected to the dehydrating decomposition reaction in the same apparatus and under the same reaction conditions as in Example 3 except that sulfuric acid was absent in the second-stage reactor. That is, the reaction took place only in the first-stage reactor.

After the lapse of 3.2 hr from the start of the reaction, $CF_3CH(OH)_2$ began to precipitate in the condenser. By that time the total amount of the feed of the hemi-acetal was 722 g (544 g as $CF_3CHO$) and the quantity of recovered $CF_3CHO$ was 529 g, so that the recovery efficiency was 97.2% by weight. In this case, 4.84 kg of sulfuric acid was used per 1 kg of the hemi-acetal.

What is claimed is:

1. A process of preparing a carbonyl compound, which is expressed by the general formula (II) and has a boiling point below room temperature under the atmospheric pressure, by dehydrating decomposition of a gem-diol, hemi-acetal or hemi-ketal expressed by the general formula (I),

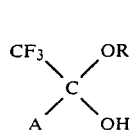

where A represents H or $CF_3$, and R represents H, $CH_3$ or $C_2H_5$,

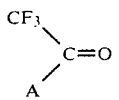

where A represents H or $CF_3$, the process being a two-stage process comprising:
    (a) as the first stage, making said gem-diol, hemi-acetal or hemi-ketal contact with sulfuric acid at a temperature in the range from 90° to 140° C. so as to partly decompose and dehydrate said gem-diol, hemi-acetal or hemi-ketal, permitting the concentration of said sulfuric acid to become lower than 93% by weight but not lower than 65% by weight; and
    (b) as the second stage, making the product of the reaction at step (a) contact with concentrated sulfuric acid at a temperature not higher than 60° C., preventing the concentration of said concentrated sulfuric acid from becoming lower than 93% by weight.

2. A process according to claim 1, wherein said temperature in step (a) is in the range from 120° to 130° C. and said temperature in step (b) is not higher than 30° C.

3. A process according to claim 1, wherein the concentration of sulfuric acid in step (a) is prevented from becoming lower than 78% by weight, and the concentration of concentrated sulfuric acid in step (b) is prevented from becoming lower than 95% by weight.

4. A process according to claim 1, wherein steps (a) and (b) are performed continuously, the process further comprising the step of (c) continuously supplying sulfuric acid to the reaction system at step (a) via the reaction system at step (b).

5. A process according to claim 1, wherein an aqueous solution of a diol expressed by the formula $(CF_3)_2C(OH)_2$ in the water-to-diol mole ratio of about 3 is brought into contact with sulfuric acid at step (a).

* * * * *